(12) United States Patent
Suzuki

(10) Patent No.: US 7,131,838 B2
(45) Date of Patent: Nov. 7, 2006

(54) DENTAL APPARATUS AND FLUID RESERVOIR FOR THE SAME

(75) Inventor: Tetsuji Suzuki, Utsunomiya (JP)

(73) Assignee: Nakanishi, Inc., Kanuma (JP)

( * ) Notice: Subject to any disclaimer, the term of this patent is extended or adjusted under 35 U.S.C. 154(b) by 199 days.

(21) Appl. No.: 10/982,825

(22) Filed: Nov. 8, 2004

(65) Prior Publication Data

US 2005/0100858 A1 May 12, 2005

(30) Foreign Application Priority Data

Nov. 7, 2003 (JP) ............................. 2003-378427

(51) Int. Cl.
*A61C 3/02* (2006.01)
*A47J 31/00* (2006.01)

(52) U.S. Cl. ............................. 433/88; 433/80; 433/84

(58) Field of Classification Search .................. 433/84, 433/88, 80; 222/402.17, 185.1; 215/307, 215/309, 310, 311, 312, 315; 601/162, 165, 601/155; 604/91, 83
See application file for complete search history.

(56) References Cited

U.S. PATENT DOCUMENTS 5,338,194 A 8/1994 Strohmaier
2003/0077552 A1 4/2003 Decosterd et al.

FOREIGN PATENT DOCUMENTS

| DE | 33 12 705 | 10/1984 |
|---|---|---|
| DE | 41 38 672 | 5/1993 |
| EP | 0 427 944 A | 5/1991 |
| JP | 3-264013 | 11/1991 |
| JP | 2000-337628 | 12/2000 |
| WO | 00/27746 | 5/2000 |

OTHER PUBLICATIONS

English Abst. DE 33 12 705 Internet.
Patent Abst. of Japan 03-264013.
Patent Abst. of Japan 2000-337628.

*Primary Examiner*—Cris L. Rodriguez
*Assistant Examiner*—Candice C. Stokes
(74) *Attorney, Agent, or Firm*—Hahn & Voight PLLC

(57) ABSTRACT

The present invention relates to dental apparatus including a fluid reservoir having a connection part, and a fluid reservoir receptor section having a reception part. The connection part includes a cylindrical member, a shaft member slidably arranged through the cylindrical member, and having a channel, a fluid passage defined between the channel and the cylindrical member, and an air passage formed in the cylindrical member for taking external air in. The openings of the fluid and air passages are openable by sliding the shaft member. The reception part includes a passage, a valve in the opening of the passage for taking external air in, and a releaser member for sliding the shaft member to open the openings of the fluid and air passages when the fluid reservoir is installed on the fluid reservoir receptor section.

7 Claims, 7 Drawing Sheets

(a)

(b)

DENTAL APPARATUS AND FLUID RESERVOIR FOR THE SAME

FIELD OF ART

The present invention relates to dental apparatus to which a dental handpiece is connected for operation, and a fluid reservoir for containing fluid to be supplied from the dental apparatus to the dental handpiece.

BACKGROUND ART

There are known a fluid reservoir for containing fluid, such as chemicals for dental treatment, and dental apparatus in which such a fluid reservoir is installed for supplying chemicals to a dental handpiece. Such a fluid reservoir and dental apparatus are disclosed in JP-2002-320628-A. The fluid reservoir disclosed in this publication has a connector piece to be fitted in a reception member of the dental apparatus, and the connector piece is provided with two one-way check valves. One of the one-way check valves has a valve ball arranged over a discharge opening of the fluid reservoir. The valve ball is biased by a spring toward a valve seat to close the discharge opening. The other of the one-way check valves also has a valve ball biased by a spring to close an aeration opening. When the fluid is drawn out of the fluid reservoir to produce negative pressure inside the reservoir, the valve ball is pushed up against the biasing force of the spring, and air is taken into the reservoir through a clearance formed between the valve ball and the valve seat to balance the internal pressure of the reservoir.

In the apparatus of JP-2002-320628-A, upon replacing the fluid reservoir, negative pressure may be produced inside the fluid reservoir. Since the fluid reservoir is provided with the aeration one-way check valve, the fluid in the reservoir may flow out through the aeration opening of the valve under the action of the negative pressure. In addition, providing two valves for one fluid reservoir disadvantageously complicates the production process since a larger number of parts are involved. Further, when the interior of the fluid reservoir is washed for repeated use, the two valves provided thereon should be opened and closed for cleaning, which is complicated and bothersome.

SUMMARY OF THE INVENTION

In the light of the foregoing problems, it is an object of the present invention to provide dental apparatus and a fluid reservoir for use in the dental apparatus that reduce the risk of fluid spill in handling the fluid reservoir, simplify the handling of the closure valve in washing the fluid reservoir, and simplify the production process of the closure valve of the fluid reservoir.

According to the present invention, there is provided dental apparatus comprising:

a fluid reservoir for containing fluid to be supplied to a dental handpiece, and having a connection part;

a fluid reservoir receptor section having a reception part for receiving said connection part of the fluid reservoir; and a line for passing the fluid from said reception part toward the dental handpiece;

said connection part of the fluid reservoir further comprising:

a cylindrical member;

a shaft member slidably arranged through the cylindrical member, and having a first axial channel formed in its outer surface;

a fluid passage for passing the fluid defined between said first axial channel and an inner surface of the cylindrical member, and having an opening located in the fluid reservoir; and an air passage formed in the cylindrical member for taking external air into the fluid reservoir, and having an opening located in the fluid reservoir;

wherein said openings of said fluid and air passages are openable by sliding the shaft member, and the shaft member is constantly thrusted to close said openings, said reception part of the fluid reservoir receptor section further comprising:

an uptake-side passage in communication with the air passage of the connection part, and having an opening;

a valve disposed in said opening of the uptake-side passage for preventing flow of the fluid or air out of the fluid reservoir and allowing external air to be taken into the fluid reservoir; and a releaser member for sliding the shaft member to open said openings of said fluid and air passages when the fluid reservoir is installed on the fluid reservoir receptor section.

In the conventional apparatus, two separate closure valves are provided, one in the fluid passage and the other in the air passage, on the side of the fluid reservoir. However, in the dental apparatus according to the present invention, the openings of both the fluid and air passages on the side of the fluid reservoir are opened and closed by the sliding action of one shaft member. Thus a fewer parts are involved in opening and closing the openings on the side of the fluid reservoir than in the conventional apparatus. This reduces the risk of fluid spill in handling the fluid reservoir, and simplifies the processes for producing the fluid reservoir and for washing the reservoir.

In the present invention, the valve for the uptake side of the air passage is located in the reception part of the fluid reservoir receptor section. Thus it is no longer necessary to provide the valve for the uptake side in each fluid reservoir, which simplifies the production process.

In the dental apparatus of the present invention, the air passage is provided in the cylindrical member, through which the shaft member is arranged to cooperatively define the fluid passage between the shaft member and the cylindrical member. Thus the openings of the fluid and air passages in the fluid reservoir may be opened and closed by the sliding action of the shaft member.

Further, in the dental apparatus of the present invention, the releaser member may optionally has a shank for pressing the shaft member to slide in the cylindrical member for opening the openings of the fluid and air passages.

According to the present invention, there is also provided a fluid reservoir for use in dental apparatus to which a dental handpiece is connected via connectors, comprising:

a connection part to be connected to a fluid reservoir receptor section of the dental apparatus, said connection part further comprising:

a cylindrical member;

a shaft member slidably arranged through the cylindrical member, and having a first axial channel formed in its outer surface;

a fluid passage for passing the fluid defined between said first axial channel and an inner surface of the cylindrical member, and having an opening; and an air passage formed in the cylindrical member for taking external air into the fluid reservoir, and having an opening;

wherein said openings of said fluid and air passages are openable by sliding the shaft member, and the shaft member is constantly thrusted to close said openings, wherein said shaft member slides in one direction to open the openings of the fluid and air passages when the fluid reservoir is installed on the fluid reservoir receptor section of the dental apparatus, whereas said shaft member slides in reverse direction to close the openings of the fluid and air passages when the fluid reservoir is detached from the fluid reservoir receptor section.

With the dental apparatus and fluid reservoir of the present invention, the risk of fluid spill in handling the fluid reservoir is reduced, handling of the closure valve in washing the fluid reservoir is simplified, and the production process of the closure valve of the fluid reservoir is simplified.

BRIEF DESCRIPTION OF THE DRAWINGS

FIG. 5 shows the shaft member constituting the connection part of the fluid reservoir according to the present invention, wherein FIG. 5(a) is a side view, partially in section, seen from arrow VIa in FIG. 5(c), FIG. 5(b) is a side view seen from arrow VIb in FIG. 5(c), and FIG. 5(c) is a cross sectional view taken along lines VIC—VIc in FIGS. 5(a) and 5(b).

FIG. 7 shows the releaser member constituting the reception part of the dental apparatus, wherein FIG. 7(a) is a side view of the releaser member seen from arrow VIIa in FIG. 7(b), and FIG. 7(b) is a top plan view of the releaser member.

PREFERRED EMBODIMENTS OF THE INVENTION

The present invention will now be explained in more detail with reference to a preferred embodiment of the present invention taken in conjunction with the attached drawings. However, the following embodiment is merely illustrative and does not intend to limit the present invention.

Figure 1:
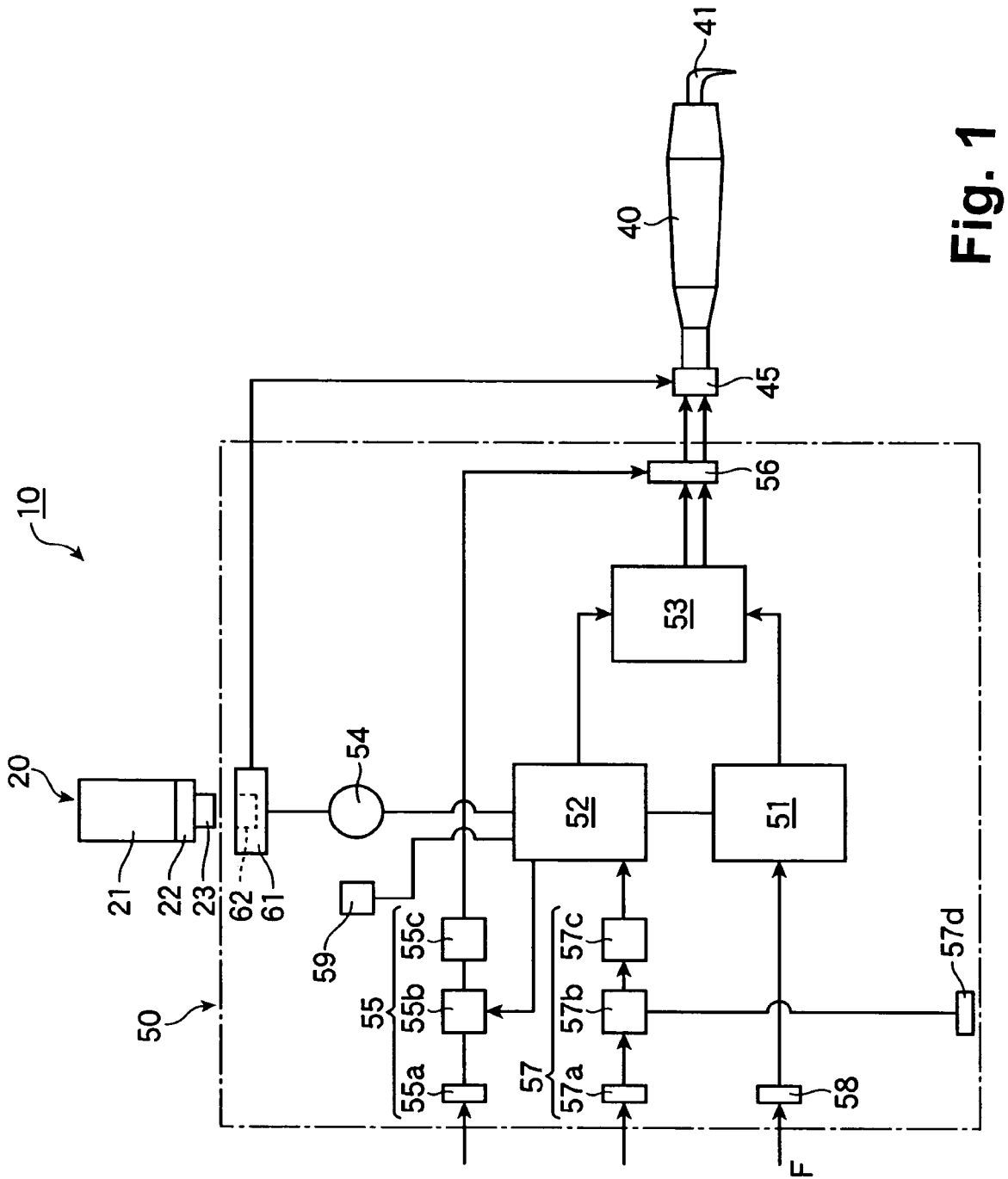
FIG. 1 is a schematic diagram illustrating the system of the dental apparatus of the present invention.
Figure 2:
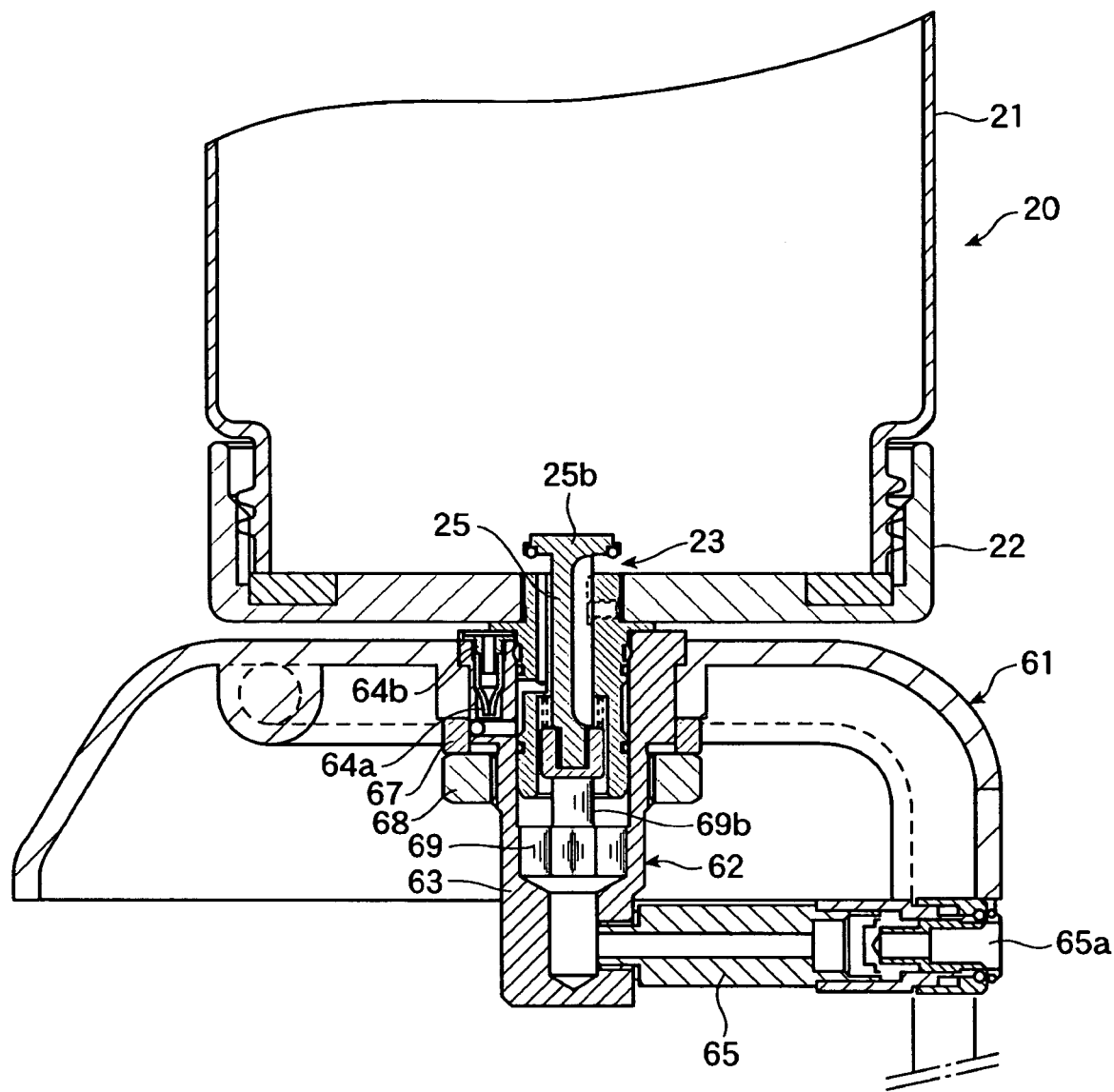
FIG. 2 is a sectional view showing the connection between the dental apparatus body and the fluid reservoir of the dental apparatus of the present invention.

Referring to FIG. 1, the dental apparatus 10 according to the present invention includes fluid reservoir 20 containing fluid, such as chemicals for dental treatment, and dental apparatus body 50, to which dental handpiece 40 is connected via connectors (not shown) such as fluid lines, electrical wiring, and tubes enclosing optical fibers or the like. As shown in FIG. 2, the fluid reservoir 20 includes bottle 21, cap 22 threaded onto and covering the opening of the bottle 21, and connection part 23 projecting from the cap 22. On the other hand, the dental apparatus body 50 has fluid reservoir receptor section 61, which has reception part 62 in a concave shape for receiving the connection part 23 of the reservoir 20.

The connection part 23 of the fluid reservoir 20 is discussed in detail.

Figure 3:
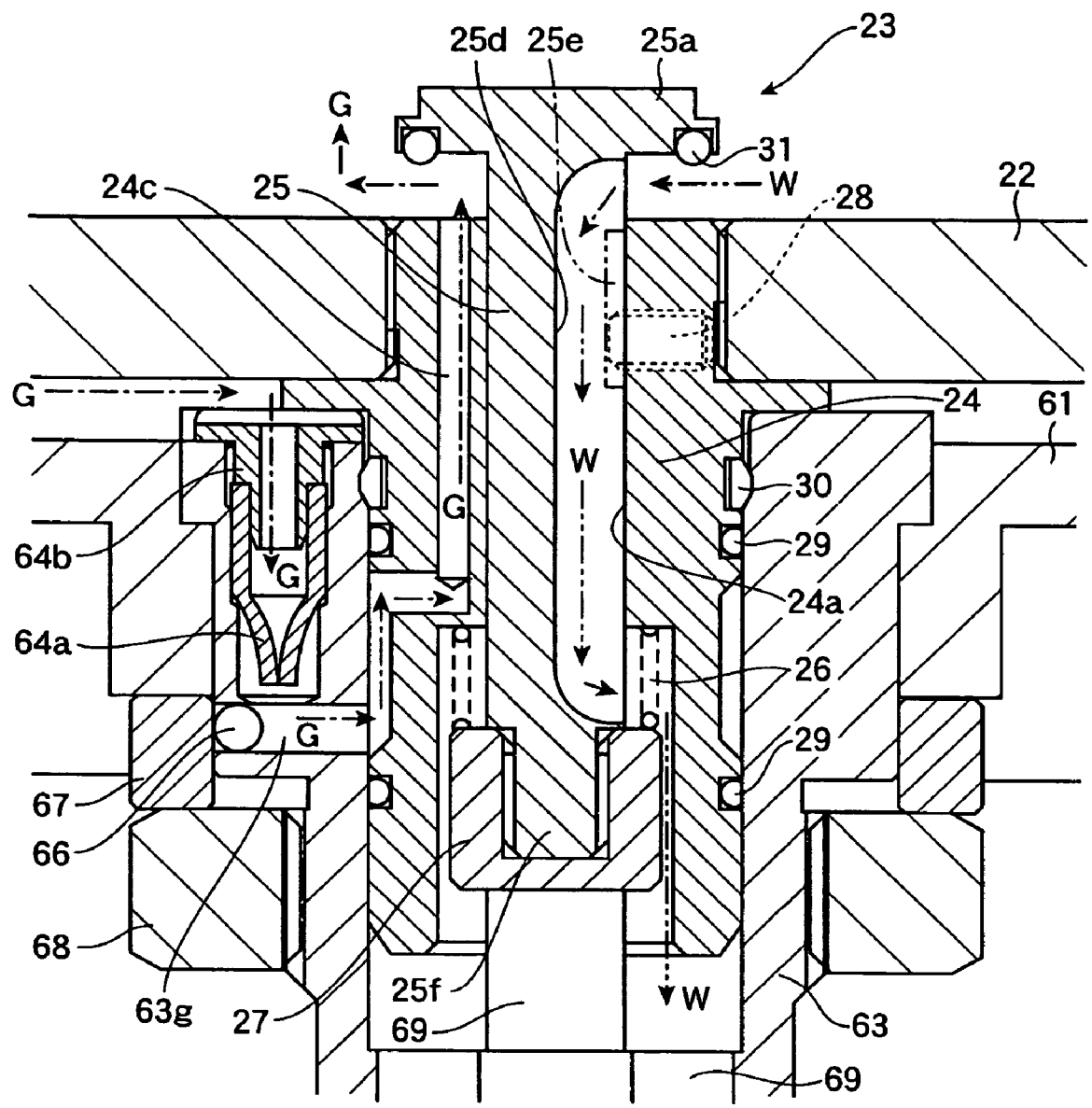
FIG. 3 is an enlarged view of the connection in FIG. 2.

Referring to FIG. 3, the connection part 23 of the fluid reservoir 20 mainly includes cylindrical member 24, shaft member 25, coil spring 26, nut 27, and stop pin 28. On the outer surface of the cylindrical member 24, O-rings 29 and stop ring 30 are fit.

Figure 4:
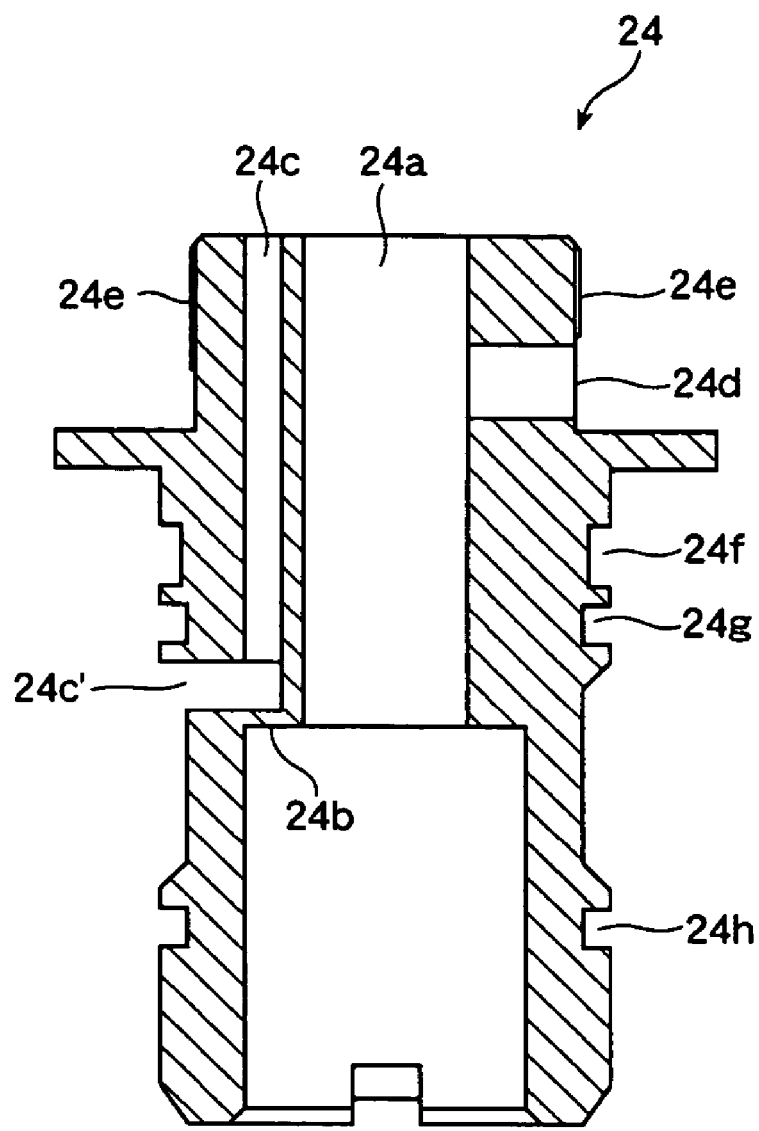
FIG. 4 is a sectional view of the cylindrical member constituting the connection part of the fluid reservoir according to the present invention.

Referring to FIG. 4, the cylindrical member 24 has a through hole 24a extending centrally and axially through the cylindrical member 24 and having step 24b in the middle to form an enlarged hole portion. In parallel to the through hole 24a, vertical hole 24c is provided in the upper part of the cylindrical member 24, which hole 24c is bent radially outwardly and ends in opening 24c'. A transverse hole 24d is provided through the outer surface of the cylindrical member 24, in communication with the through hole 24a. On the outer surface of the cylindrical member 24, threads 24e are provided in the upper end portion of the member 24 for being screwed in the cap 22, annular groove 24f is provided, in which the stop ring 30 is fit, and annular grooves 24g and 24h are provided, in which O-rings 29 are fit, respectively. The step 24b of the through hole 24a, as shown in FIG. 3, is formed so that the upper end of the coil spring 26 abuts the step 24b, and the lower enlarged hole portion of the through hole 24a below the step 24b accommodates the nut 27.

Figure 5:
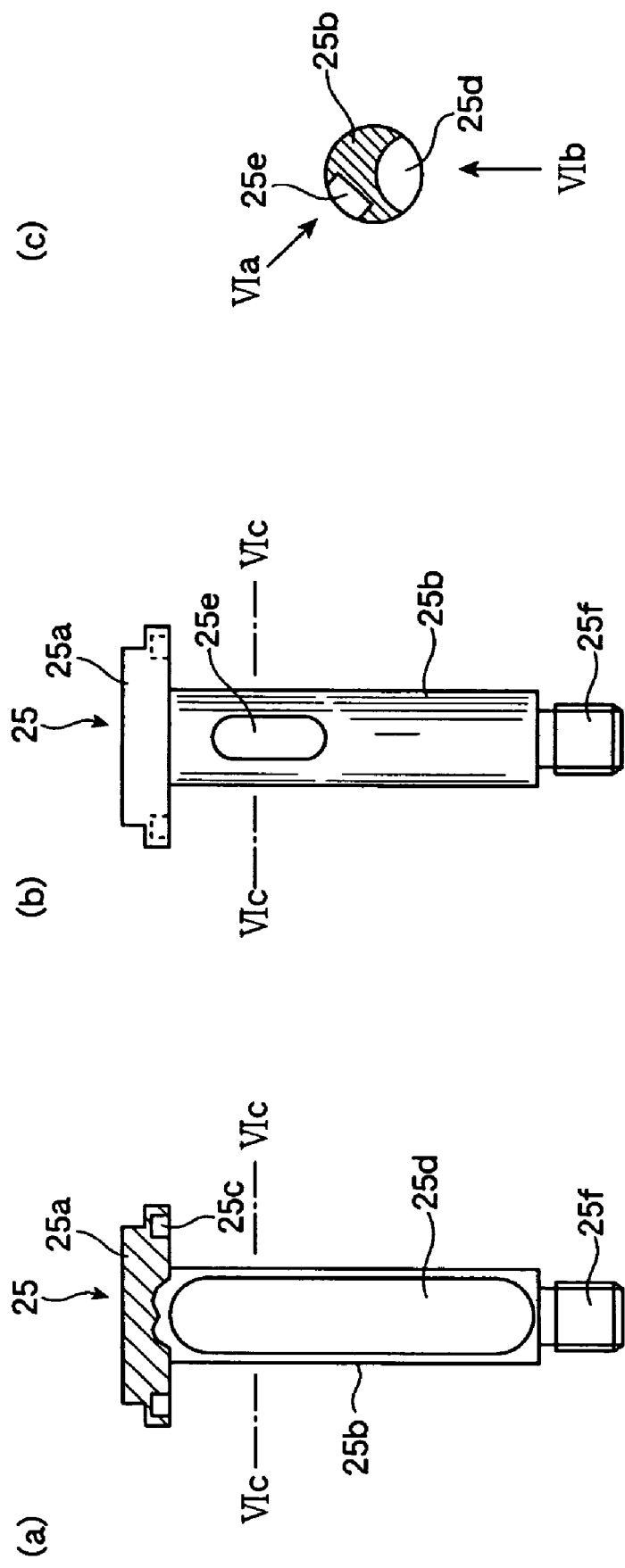

Referring to FIG. 5, the shaft member 25 has shank 25b extending axially, and flange 25a integrally formed on the top of the shank 25b. The flange 25a has groove 25c in its lower surface to fit O-ring 31 therein. The shank 25b has axial channel 25d formed in its outer surface over almost its entire length, and a short slot 25e, which is shorter than the axial channel 25d, and provided also in the outer surface of the shank 25b in a different circumferential position from the channel 25d. The shank 25b has lower part 25f having threads on its surface, onto which the nut 27 is screwed.

Referring to FIG. 3, the connection part 23 is assembled by fitting the O-ring 31 in the groove 25c on the flange 25a of the shaft member 25, inserting the shank 25b of the shaft member 25 into the through hole 24a of the cylindrical member 24, placing the coil spring 26 around the lower portion of the shank 25b, and threading the nut 27 onto the lower part 25f so that the coil spring 26 is compressed and confined between the nut 27 and the step 24b. The stop pin 28 is inserted into the transverse hole 24d of the cylindrical member 24 and into the short slot 25e of the shaft member 25 to prevent the shaft member 25 from rotating around its axis with respect to the cylindrical member 24. The assembled connection part 23 is then connected to the cap 22 of the fluid reservoir 20 by threading the upper part 24e of the cylindrical member 24 into the cap 22. Further, the O-rings 29 are fit in the annular grooves 24g and 24h and the stop ring 30 in the groove 24f on the outer surface of the cylindrical member 24.

With the structure discussed above, the space defined between the axial channel 25d of the shaft member 25 and the inner surface of the through hole 24a of the cylindrical member 24 functions as a passage for the fluid in the fluid reservoir 20. On the other hand, the vertical hole 24c of the cylindrical member 24 functions as a passage for taking external air into the fluid reservoir 20. In FIG. 2, the fluid reservoir 20 is attached to the reception part 62, so that the shaft member 25 is shown slightly pressed up. However, when the fluid reservoir 20 is not attached to the reception part 62, the shaft member 25 is thrusted downwards by means of the coil spring 26, which brings the O-ring 31 on the flange 25a into tight contact with the upper end surface of the cylindrical member 24, so that the openings of the fluid passage and the passage for the external air are closed.

Next, the reception part 62 of the dental apparatus body 50 is now explained.

As shown in FIG. 2, the reception part 62 mainly includes casing 63, valve 64a, and releaser member 69.

Figure 6:
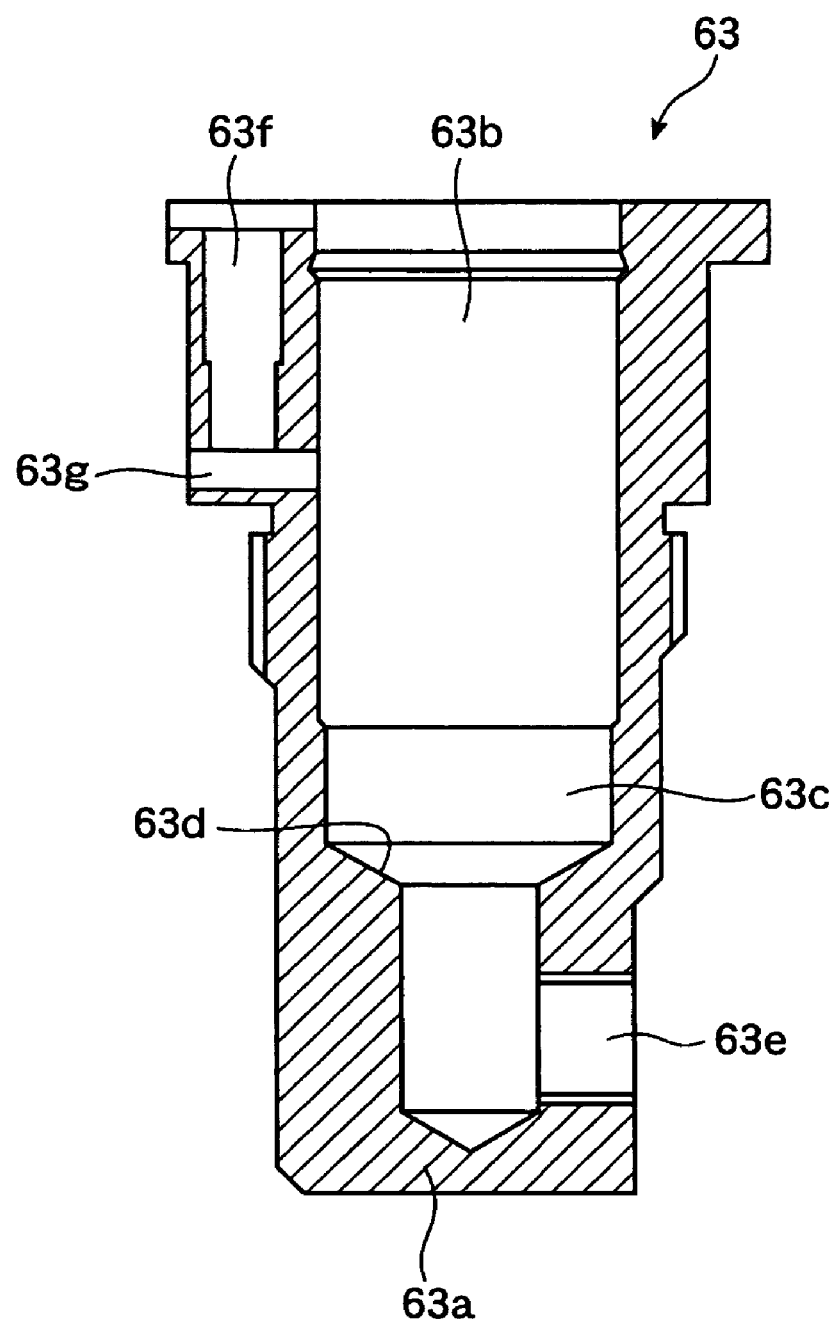
FIG. 6 is a sectional view of a member constituting the reception part of the dental apparatus according to the present invention.

Referring to FIG. 6, the casing 63 has an axial hole 63b provided in the casing 63 leaving the bottom 63a. In the middle of the axial hole 63b, the diameter of the hole 63b is slightly reduced from that of the upper portion of the hole 63b to form reduced diameter section 63c with a step between the upper section of the axial hole 63b and the reduced diameter section 63c. Below the reduced diameter section 63c, tapered section 63d is provided, below which a further reduced diameter section is formed. A transverse hole 63e extends through the outer surface of the casing 63 in its lower end part to communicate with the axial hole 63b in the further reduced diameter section. In the upper part of the casing 63, valve seat 63f in the form of an axial hole is provided, and transverse hole 63g extends through the outer surface of the casing 63 across the bottom of the valve seat 63f into the axial hole 63b. In this valve seat 63f, as shown in FIG. 3, valve 64a is fit and fixed with valve fixing means 64b. As shown in FIG. 2, the casing 63 is fit in the fluid reservoir receptor section 61 with packing 66 (FIG. 3) being fit in the transverse hole 63g, and fixed to the receptor section 61 with first and second fixing means 67 and 68. Connector tube 65 is connected at one end to the transverse hole 63e, and opening 65a of the connector tube 65 at the other end is connected to a tube pump (not shown).

Figure 7:
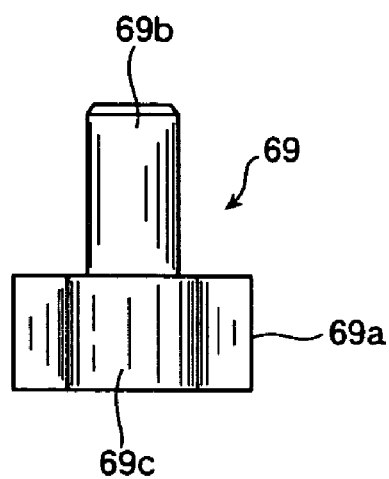
Figure 7:
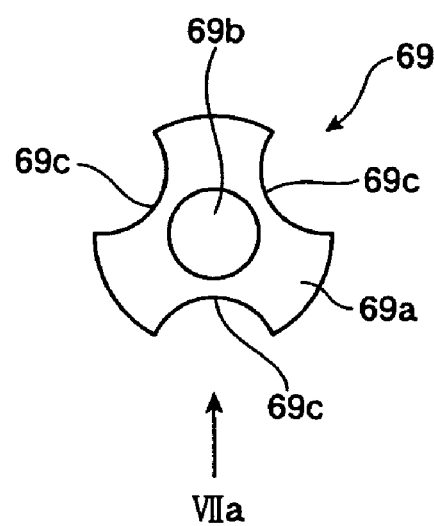

Referring to FIG. 7, the releaser member 69 has base 69a having three cut-outs 69c having arc sections, and shank 69b extending axially upwardly from the base 69a. This releaser member 69 is placed in the casing 63, with the base 69a being fit in the reduced diameter section 63c. In this state, the space defined by each cut-out 69c and the inner surface of the reduced diameter section 63c functions as a fluid passage.

The operation of the apparatus when the fluid reservoir 20 is installed on the fluid reservoir receptor section 61 is now discussed.

As shown in FIG. 2, when the connection part 23 of the fluid reservoir 20 is inserted into the reception part 62 of the receptor section 61, the lower end of the shaft member 25, i.e., the bottom of the nut 27 threaded on the lower part 25f of the shaft member 25, abuts the shank 69b of the releaser member 69, and is pushed upwardly with respect to the cylindrical member 24 against the thrusting force of the coil spring 26, which is now compressed accordingly. This brings the flange 25a of the shaft member 25 out of contact with the upper end surface of the cylindrical member 24 to release the closure of the openings of the fluid passage and the passage for the external air on the side of the fluid reservoir. Thus the fluid in the fluid reservoir 20 is allowed to flow, as shown by chain double-dashed arrow W in FIG. 3, through an opening between the flange 25a and the opening of the cylindrical member 24 downwardly into the passage defined by the axial channel 25d of the shaft member 25 and the inner surface of the through hole 24a of the cylindrical member 24, further through the passages defined by the cut-outs 69c of the releaser member 69 and the inner surface of the reduced diameter section 63c of the casing 63, and then through the connector tube 65 and its opening 65a into the tube pump.

When the fluid is pumped out of the fluid reservoir 20 in this manner, negative pressure is generated in the bottle 21, which causes the valve 64a to open. External air is flown into the opened valve 64a, as shown by chain dashed arrow G in FIG. 3, then through the transverse hole 63g of the casing 63, upwardly through the vertical hole 24c of the cylindrical member 24, and into the bottle 21 through an opening below the flange 25a. The air is taken in until the internal pressure of the fluid reservoir 20 is sufficiently lowered.

Finally, the system of the dental apparatus body 50 is discussed with reference to FIG. 1.

The dental apparatus body 50 mainly includes control substrate 51, power and pump substrate 52, oscillation substrate 53, pump motor 54, and water supply line 55.

The control substrate 51 is provided with operation circuits for transmitting signals from operation buttons to microcomputer circuits, microcomputer circuits for ON/OFF control of other circuits in response to signal F received through terminal 58 from a foot switch as well as signals from the operation circuits, and display circuits for displaying the operation status of the microcomputer circuits by means of LEDs.

The power and pump substrate 52 is provided with pump control circuits for controlling the pump motor 54 in response to signals from motor speed adjusting device 59 and the microcomputer circuits, electromagnetic valve control circuits for opening and closing electromagnetic valve 55b in response to signals from the microcomputer circuits, and main power supply circuits for supplying power to each circuit. Electric pathway 57 to the main power supply circuits transmits electricity through AC inlet 57a, open/close switch 57b, and power transformer 57c into the main power supply circuits. The open/close switch 57b is switched ON/OFF by means of power switch 57d, and the power input is stepped down to a predetermined voltage by means of the power transformer 57c.

The oscillation substrate 53 is provided with light power supply circuits for switching ON/OFF a light built in the dental handpiece 40, and ultrasonic transmitter circuits for performing sweep oscillation to search for the resonance point of an electrostriction transducer built in the dental handpiece 40 and tip 41, and locking at the resonance point once it is found in the second cycle. Signals from the light power supply circuits and the ultrasonic transmitter circuits are output via output terminal 56.

The water supply line 55 supplies water, such as tap water, to the dental handpiece 40, and includes terminal 55a for taking water into the line, electromagnetic valve 55b, water control valve 55c, and output terminal 56, in series.

When uptake of water into the water supply line 55 is selected, the electromagnetic valve control circuits of the power and pump substrate 52 are activated to open/close the electromagnetic valve 55b in response to ON/OFF of the foot switch. The amount of water is adjusted with the water control valve 55c, and a suitable amount of water is introduced into the dental handpiece 40 through the output terminal 56 and junction connector 45, and injected through the injection nozzle located at the tip of the handpiece 40.

On the other hand, when uptake of the liquid, such as chemicals, contained in the fluid reservoir 20 is selected, the pump control circuits of the power and pump substrate 52 are activated to start/stop the rotation of the pump motor 54 in response to ON/OFF of the foot switch. The pump motor 54 presses the tube pump to inject the liquid due to the pressure change therein. The amount of the liquid is adjusted by increasing/decreasing the rotation speed of the pump motor 54 with the pump control circuits, which is operated by the motor speed adjusting device 59. The liquid discharged from the tube pump is lead to the junction connector 45 and supplied to the dental handpiece 40. In the junction connector 45, a check valve is provided both on the input side of the liquid from the fluid reservoir 20 and on the input side of water, such as tap water, to prevent backflow of the liquid and water.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. Dental apparatus comprising:
   a fluid reservoir for containing fluid to be supplied to a dental handpiece, and having a connection part;
   a fluid reservoir receptor section having a reception part for receiving said connection part of the fluid reservoir; and
   a line for passing the fluid from said reception part toward the dental handpiece;
   said connection part of the fluid reservoir further comprising:
      a cylindrical member;
      a shaft member slidably arranged through the cylindrical member, and having a first axial channel formed in its outer surface;
      a fluid passage for passing the fluid defined between said first axial channel and an inner surface of the cylindrical member, and having an opening located in the fluid reservoir; and
      an air passage formed in the cylindrical member for taking external air into the fluid reservoir, and having an opening located in the fluid reservoir;
      wherein said openings of said fluid and air passages are openable by sliding the shaft member, and the shaft member is constantly thrusted to close said openings,
   said reception part of the fluid reservoir receptor section further comprising:
      an uptake-side passage in communication with the air passage of the connection part, and having an opening;
      a valve disposed in said opening of the uptake-side passage for preventing flow of the fluid or air out of the fluid reservoir and allowing external air to be taken into the fluid reservoir; and
      a releaser member for sliding the shaft member to open said openings of said fluid and air passages when the fluid reservoir is installed on the fluid reservoir receptor section.

2. The dental apparatus of claim 1, wherein said releaser member comprises a shank for abutting an end of the shaft member located outside of the fluid reservoir, said shank pressing the shaft member to slide in the cylindrical member for opening the openings of the fluid and air passages.

3. The dental apparatus of claim 1, wherein said releaser member has a plurality of cut-outs acting as fluid passages.

4. A fluid reservoir for use in dental apparatus to which a dental handpiece is connected via connectors, comprising:
   a connection part to be connected to a fluid reservoir receptor section of the dental apparatus,
   said connection part further comprising:
   a cylindrical member;
   a shaft member slidably arranged through the cylindrical member, and having a first axial channel formed in its outer surface;
   a fluid passage for passing the fluid defined between said first axial channel and an inner surface of the cylindrical member, and having an opening; and
   an air passage formed in the cylindrical member for taking external air into the fluid reservoir, and having an opening;
   wherein said openings of said fluid and air passages are openable by sliding the shaft member, and the shaft member is constantly thrusted to close said openings,
   wherein said shaft member slides in one direction to open the openings of the fluid and air passages when the fluid reservoir is installed on the fluid reservoir receptor section of the dental apparatus, whereas said shaft member slides in reverse direction to close the openings of the fluid and air passages when the fluid reservoir is detached from the fluid reservoir receptor section.

5. The fluid reservoir of claim 4, further comprising means for thrusting the shaft member including:
   a flange provided on a lower end of the shaft member;
   a step formed in the cylindrical member, facing to said flange; and
   a spring disposed between said flange and said step.

6. The fluid reservoir of claim 4, wherein said shaft member has a second channel shorter than the first channel, for restricting rotation of the shaft member in the cylindrical member, wherein said cylindrical member has a hole located facing to said second channel, wherein a pin is inserted through said hole into said second channel.

7. The fluid reservoir of claim 4, wherein said shaft member has a flange formed on an upper end of the shaft member for closing the openings of the fluid and air passages when the fluid reservoir is detached from the fluid reservoir receptor section.

* * * * *